(12) United States Patent
Peters

(10) Patent No.: US 9,186,269 B2
(45) Date of Patent: Nov. 17, 2015

(54) ANKLE BRACE INCLUDING A SNAP-TOGETHER PIVOTING UPPER EXTENSION SHELL

(75) Inventor: Rick Peters, Indianapolis, IN (US)

(73) Assignee: Ultra Athlete LLC, Indianapolis, IN (US)

( * ) Notice: Subject to any disclaimer, the term of this patent is extended or adjusted under 35 U.S.C. 154(b) by 317 days.

(21) Appl. No.: 13/527,653

(22) Filed: Jun. 20, 2012

(65) Prior Publication Data

US 2013/0345613 A1    Dec. 26, 2013

(51) Int. Cl.
*A61F 5/01* (2006.01)
(52) U.S. Cl.
CPC ................. *A61F 5/01* (2013.01); *A61F 5/0127* (2013.01)

(58) Field of Classification Search
USPC ........................... 602/27–29, 23–24; 128/882
See application file for complete search history.

(56) References Cited

U.S. PATENT DOCUMENTS

| | | | | |
|---|---|---|---|---|
| 582,192 | A | * | 5/1897 | Entrekin .......................... 602/16 |
| 4,632,096 | A | * | 12/1986 | Harris .............................. 602/16 |
| 6,390,998 | B1 | * | 5/2002 | Doyle .............................. 602/26 |
| 6,955,654 | B2 | * | 10/2005 | Gilmour .......................... 602/16 |
| 7,524,295 | B1 | * | 4/2009 | Peters et al. ...................... 602/5 |
| 7,572,241 | B2 | * | 8/2009 | Slautterback et al. .......... 602/23 |

* cited by examiner

*Primary Examiner* — Ophelia A Hawthorne
(74) *Attorney, Agent, or Firm* — Camoriano and Associates

(57) ABSTRACT

An ankle brace includes an upper extension shell pivotably connected to and projecting upwardly from the medial shell along left and right lateral was by first and second snap-together pivot means.

10 Claims, 7 Drawing Sheets

ANKLE BRACE INCLUDING A SNAP-TOGETHER PIVOTING UPPER EXTENSION SHELL

BACKGROUND

The present invention relates to an ankle brace. More particularly, it relates to an ankle brace that can be converted for use at different stages of treatment of an ankle.

U.S. Pat. No. 7,524,295 "Peters et al." discloses a convertible ankle brace which may be used in one configuration, including an upper extension shell, for providing substantial support to treat an acutely injured ankle and then, after the ankle has improved, the upper extension shell can be removed, and the brace can be used during normal athletic activities to protect against future injury.

One embodiment provides for the upper extension shell to connect to the medial shell with a snap-fit connection that rigidly secures the upper extension shell to the medial shell in order to provide an increased level of support and stability.

SUMMARY

The present invention is similar to the ankle brace having an upper extension shell with a static snap-fit connection disclosed in the '295 Peters patent, but it improves over that arrangement by using snap-fit connections which allow pivoting motion between the upper extension shell and the medial shell so the ankle brace can comfortably and securely conform to the user's anatomy.

DESCRIPTION

Figure 1:
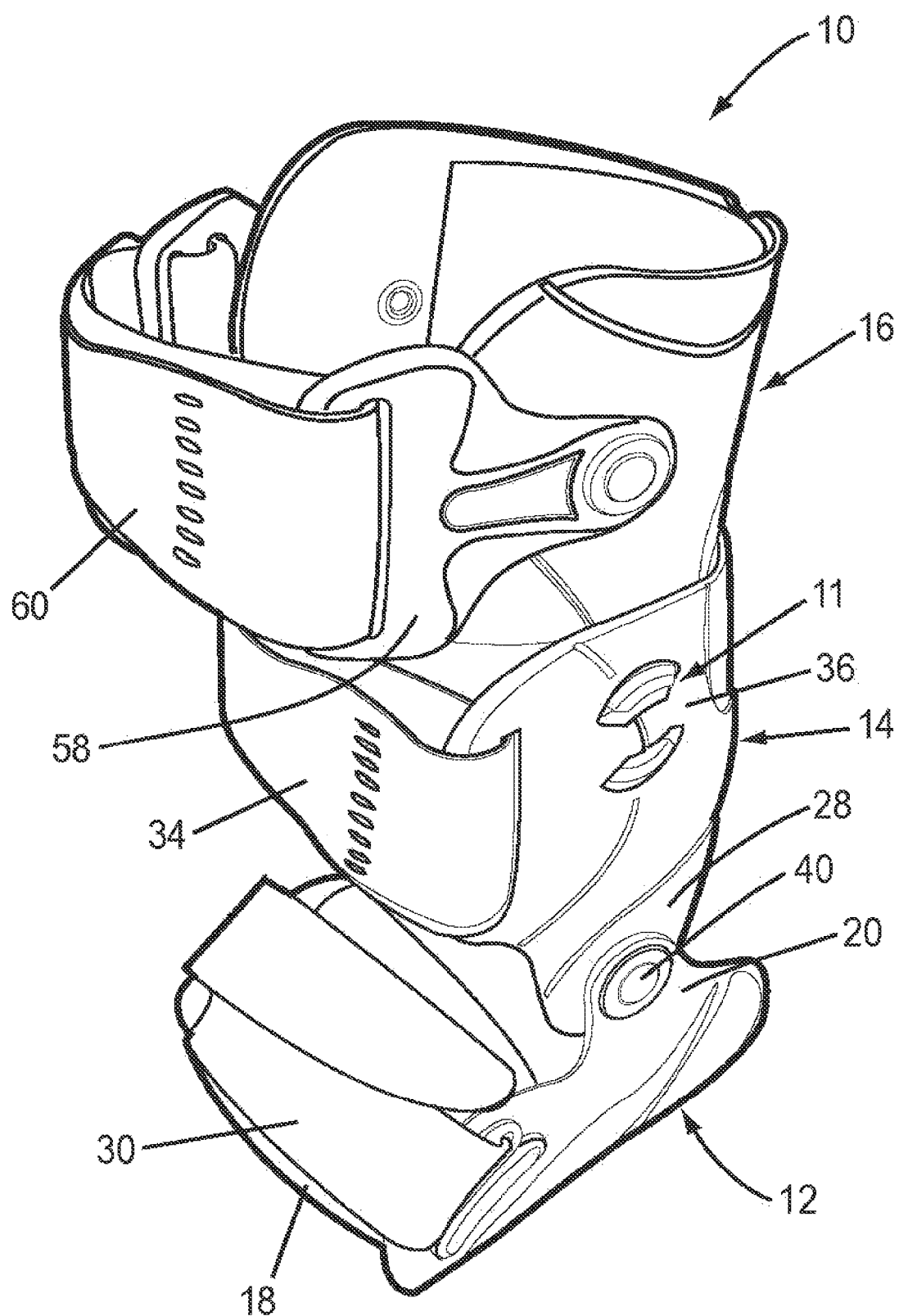
FIG. 1 is a perspective view of an ankle brace with dynamic snap-fit connections.
Figure 2:
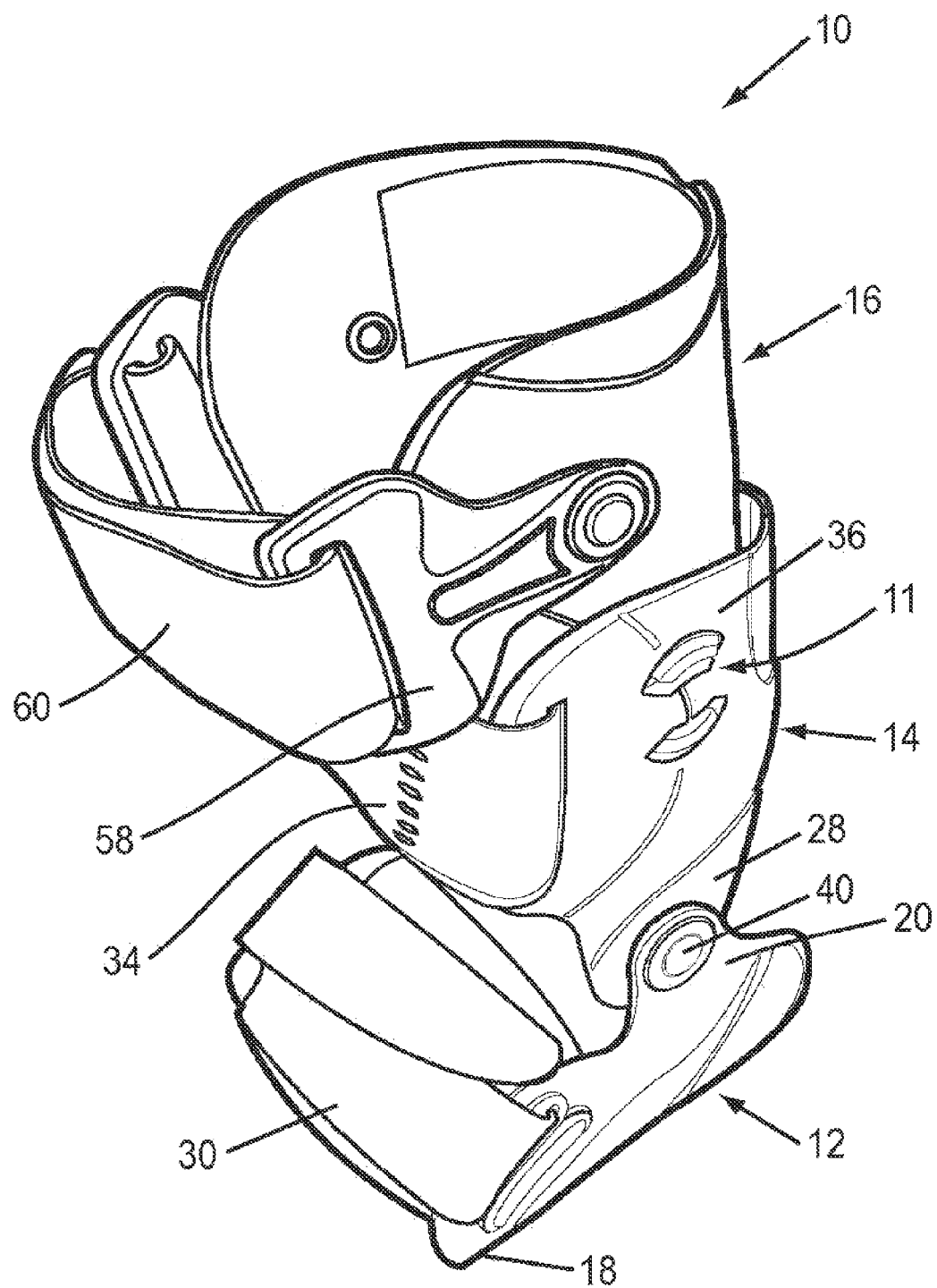
FIG. 2 is a perspective view of the ankle brace of FIG. 1 with the upper extension shell pivoted forward.
Figure 3:
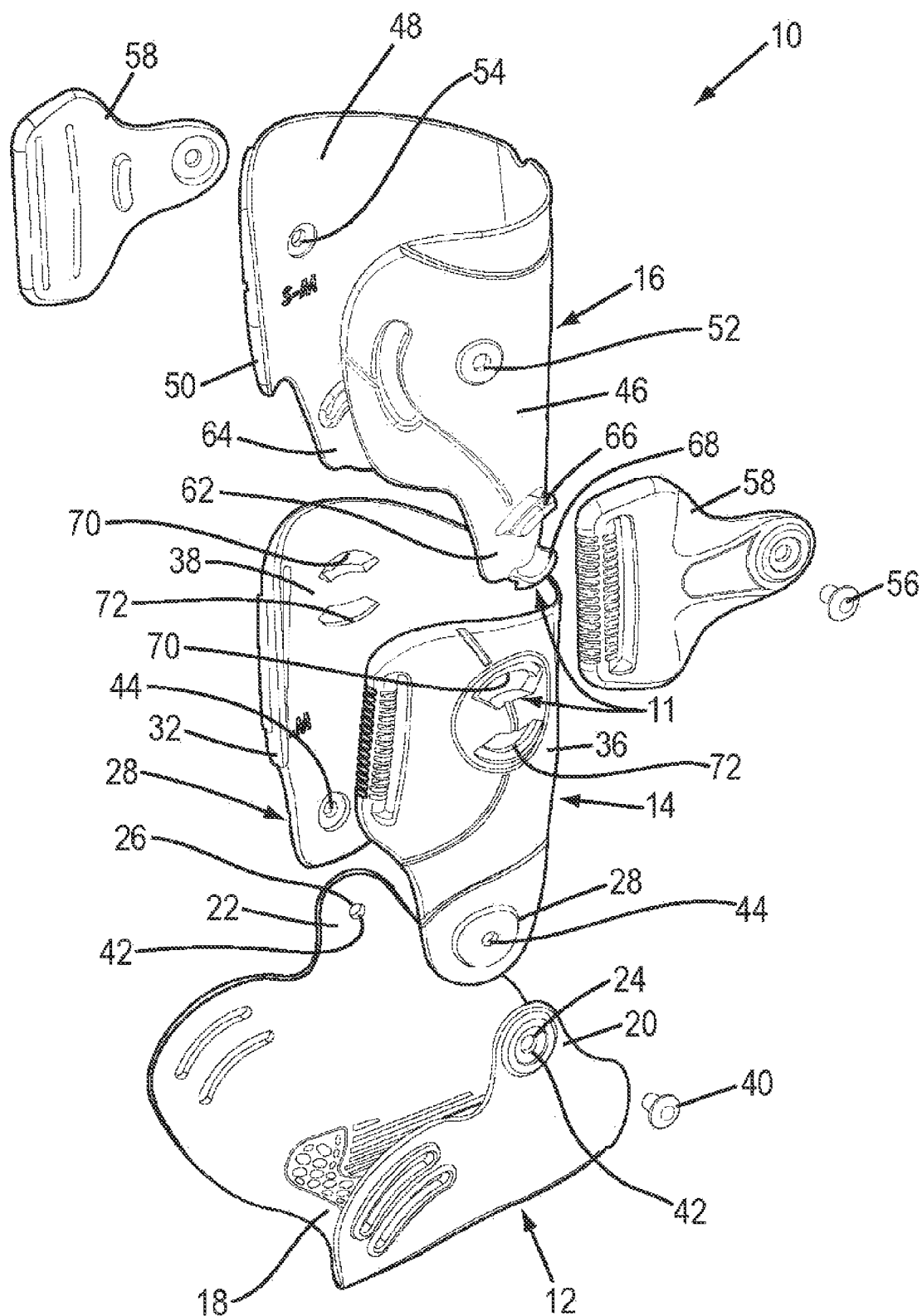
FIG. 3 is an exploded, perspective view of the ankle brace of FIG. 1, with the straps omitted for clarity.

FIGS. 1-7 show an ankle brace 10 with pivoting snap-fit connections 11. Referring to FIGS. 1-3, the ankle brace 10 includes a foot shell 12, a medial shell 14, and an upper extension shell 16.

The foot shell 12 includes a base portion 18 that underlies the user's foot and includes a substantially flat extension which projects forward to just beyond the arch of the foot when the brace is worn by the user. The foot shell 12 has a contoured stirrup shape and includes left and right side portions 20, 22, respectively, extending upwardly from the base 18. Each of these side portions 20, 22 is connected to the lower extension 28 of the respective lateral wall 36, 38 of the medial shell 14 by means of a respective lower pivot connection 24, 26. These pivot connections 24, 26 allow pitch motion of the foot shell 12 relative to the medial shell 14, to allow replication of the foot motion at the ankle during normal walking activities while providing support to prevent undesired motions.

Each of the lower pivot connections 24, 26 provides for pivoting about a left-to-right pivot axis. In this embodiment, the ankle brace is symmetrical, so the left and right lower pivot connections 24, 26 both pivot about the same left-to-right axis.

A strap 30, which extends through openings in the foot shell 12, secures the foot shell 12 to the wearer's foot.

The medial shell 14 has a substantially "U" shaped cross section, including a posterior portion integral with and connecting the respective lateral walls 36, 38. It is designed to fit against, and is contoured to, both lateral sides and the posterior side of the lower leg, and is open at the anterior side 32. A strap 34 adjacent the anterior side 32 extends through openings in the medial shell to secure the medial shell 14 to the lower end of the wearer's leg, above the ankle. Upper left and right pivoting snap-fit connections 11, described in more detail later, connect the lateral walls 36, 38 of the medial shell 14 to the respective upper left and right lateral walls of 46, 48 of the upper extension shell 16. While only the left snap-fit connection 11 can be seen, it is understood that the ankle brace 10 is symmetrical about an imaginary vertical, front-to-back plane, so the right snap-fit connection 11 is the same as the left snap-fit connection 11.

The left and right snap-fit connections 11 also may be referred to as first and second snap-together pivot means.

Referring to FIG. 3, the side portions 20, 22 of the foot shell 12 overlap the lower extensions 28 of the lateral walls 36, 38 of the medial shell 14, and rivets 40 extending through aligned openings 42 (in the foot shell 12) and 44 (in the medial shell 14) pivotably secure the foot shell 12 to the medial shell 14 to form the lower pivot connections 24, 26. These connections 24, 26 allow pitch movement of the foot relative to the ankle.

The upper extension shell 16 also has a substantially "U" shaped cross section, similar to the medial shell 14. On the upper extension shell 16 both lateral walls 46, 48 define openings 52, 54 towards the anterior side 50. Rivets 56 extend through those openings 52, 54 and pivotably secure buckles 58 to the upper extension shell 16. A strap 60, threaded through the buckles 58, secures the upper extension shell 16 to the wearer's leg.

The lateral walls 46, 48 of the upper extension shell 16 include downwardly-projecting tabs 62, 64. Each of these tabs 62, 64 defines upper and lower outwardly-extending arcuate projections 66, 68, respectively (See also FIG. 4) which are received by, and cooperate with, corresponding slotted openings 70, 72 to form the pivoting snap-fit connections 11, as described below.

Figure 5:
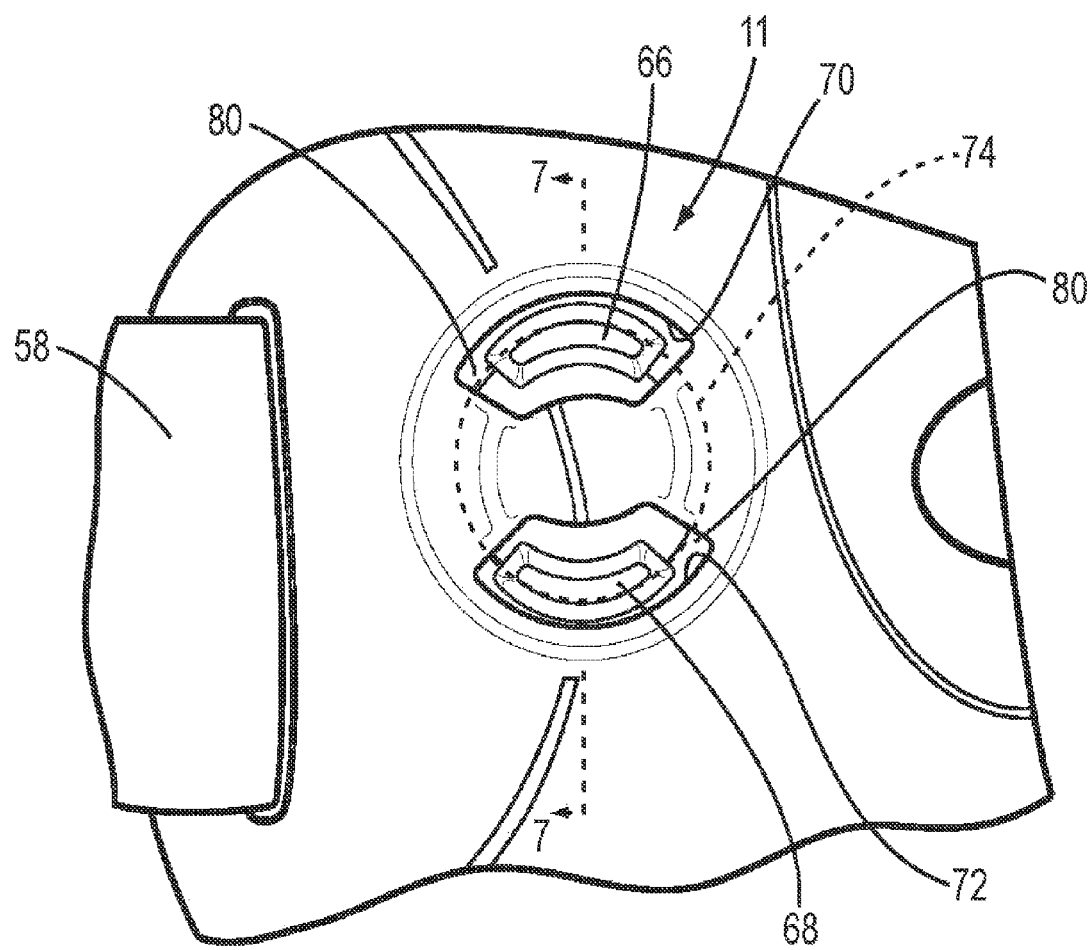
FIG. 5 is a broken away, enlarged side view of the snap-fit connection of FIG. 1.

It should be noted that both the projections 66, 68 (on the upper extension shell 16) and the openings 70, 72 (on the medial shell 14) in which the projections 66, 68 are received define arcs which lie on an imaginary circle 74 (See FIG. 5). That is, the arc on the projections 66, 68 defines a circle 74, and the arc on the openings 70, 72 also defines the same circle 74. The left-to-right pivot axis for each pivot connection 11 extends through the center of the imaginary circle 74.

In this embodiment, both pivot connections 11 pivot about the same left-to-right pivot axis. Also, in this embodiment, the pivot axes of the snap-together pivot connections 11 lie directly above the pivot axes of the lower pivot connections 24, 26, so both the upper pivot axes and the lower pivot axes lie in the same imaginary left-to-right vertical plane.

It may be appreciated that the openings 70, 72 extend farther around the imaginary circle (for a greater arcuate distance) than do the projections 66, 68, so the projections 66, 68 can rotate within the openings 70, 72 for a limited degree of rotation of the upper extension shell 16 relative to the medial shell 14. This provides a means for restricting the amount of rotation. In this particular embodiment, each of the openings 70, 72 extends for an arc of 110 degrees, while each of the projections 66, 68 extends for an arc of 80 degrees, which permits the projections 66, 68 to pivot forwardly 15 degrees and rearwardly 15 degrees from a neutral, centered position, or a total amount of 30 degrees of pivot. It is preferred for the snap-together pivot connection to restrict the total amount of rotation to a maximum not greater than 60 degrees and that the total amount of rotation permitted by the snap-together pivot connection be at least 10 degrees. Also, in this embodiment, the projections 66, 68 lie directly opposite each other and the openings 70, 72 lie directly opposite each other at the top and bottom of the imaginary circle.

Figure 6:
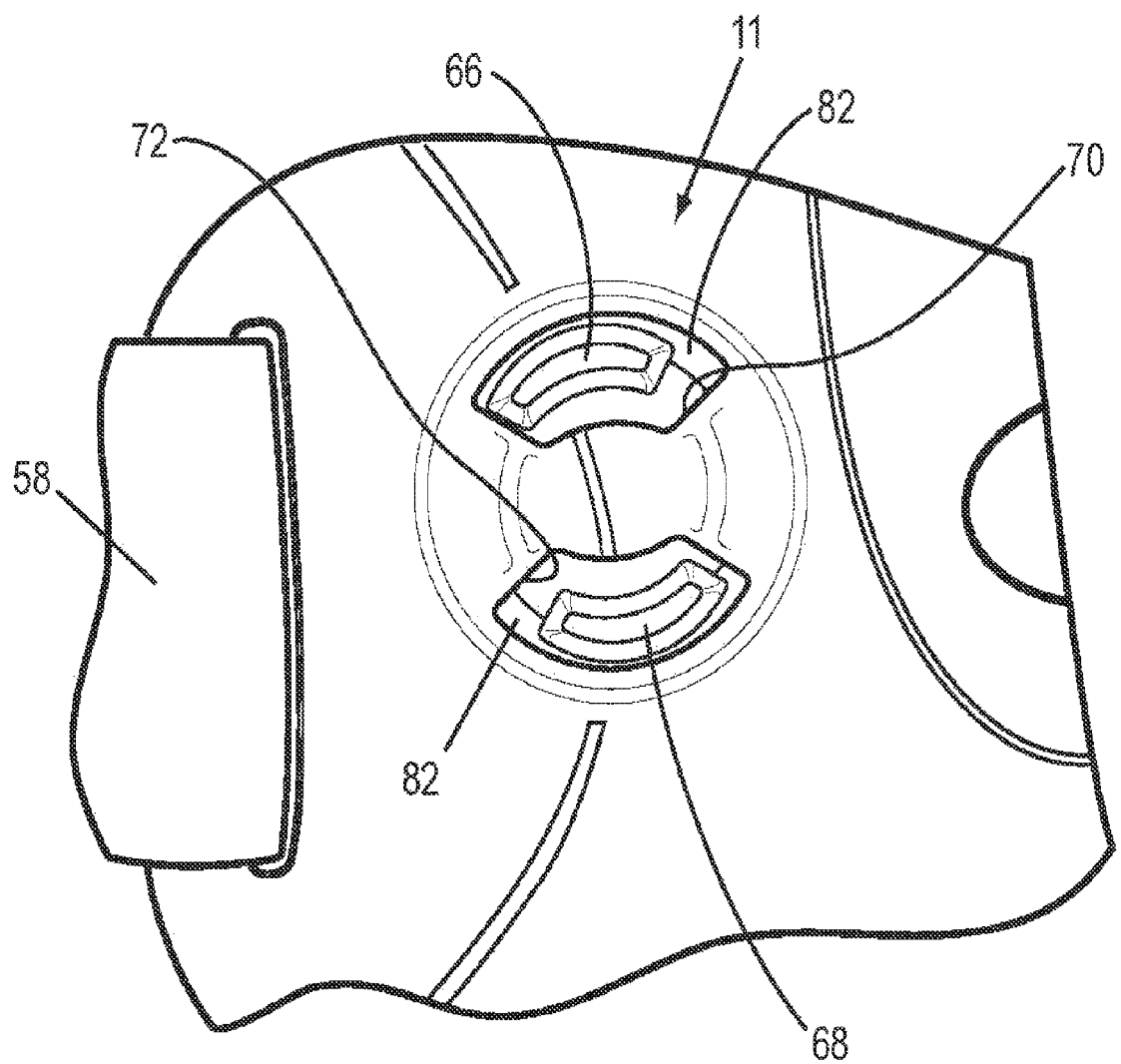
FIG. 6 is the same view as FIG. 5 but with the upper extension shell pivoted forward as in FIG. 2.

The rotation of the upper extension shell 16 relative to the medial shell 14 can be seen by comparing the views of FIGS. 5 and 6. In FIG. 5, the upper extension shell 16 is substantially in a straight-up, non-pivoted position relative to the medial shell 14. In FIG. 6, the upper extension shell 16 is in a pivoted forward position relative to the medial shell 14, with the forward end of the upper projection 66 abutting the forward end of the upper slot 70, and the rearward end of the lower projection 68 abutting the rearward end of the lower slot 72. There is also a pivoted rearward position, which is not shown, in which the rearward end of the upper projection 66 abuts the rearward end of the upper slot 70, and the forward end of the lower projection 68 abuts the forward end of the lower slot 72.

Figure 4:
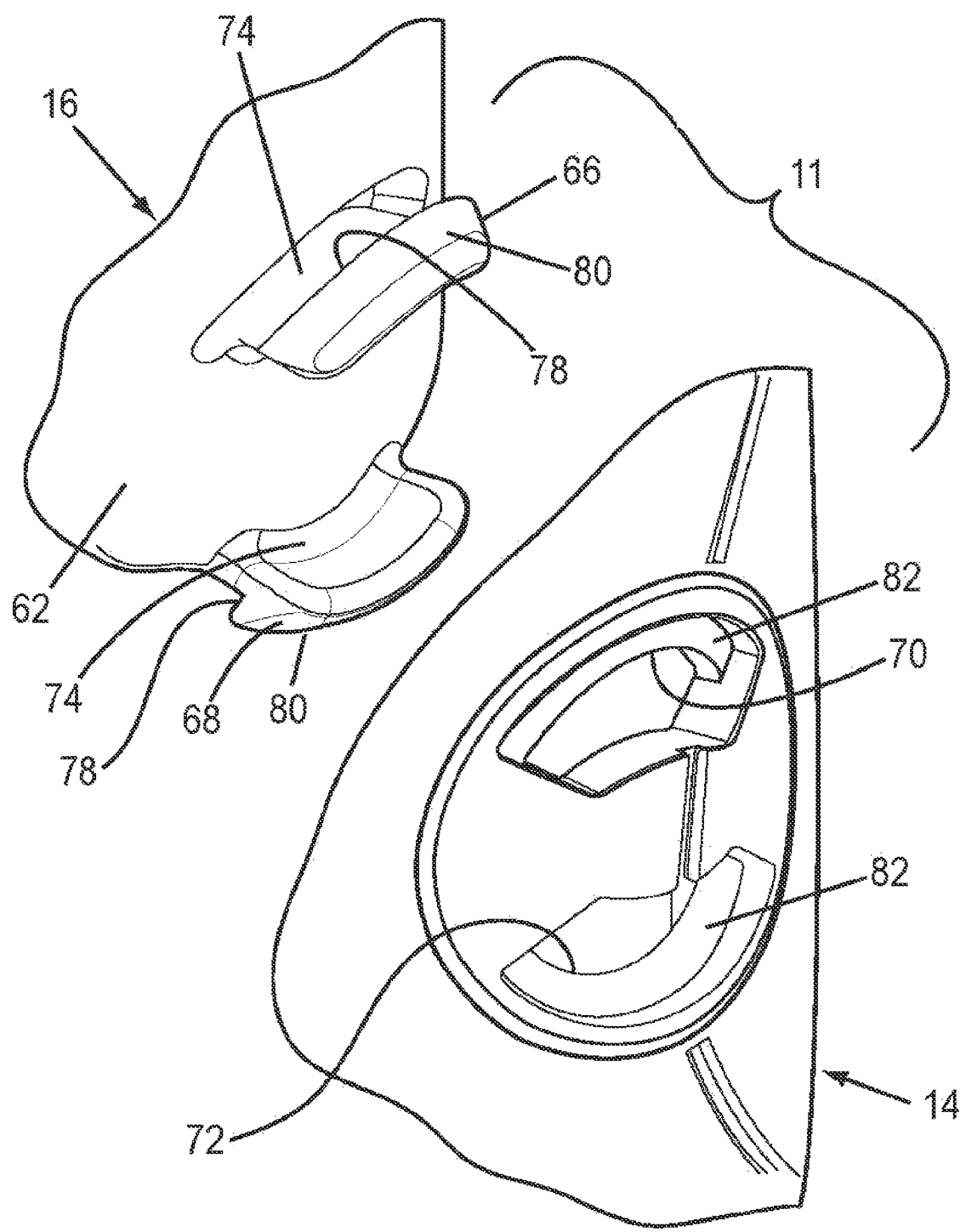
FIG. 4 is a broken away, enlarged, perspective view of the snap-fit connection of FIG. 3.
Figure 7:
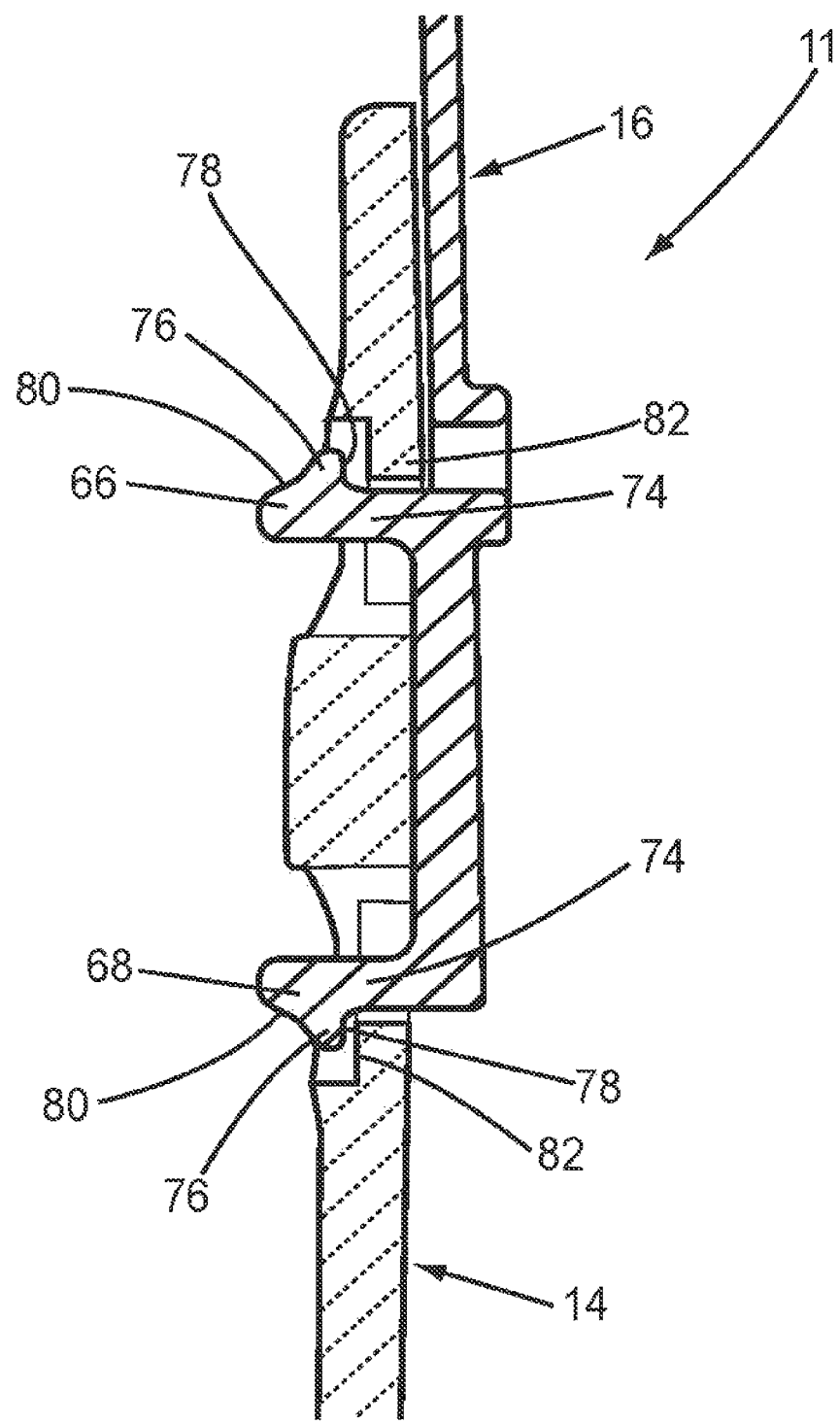
FIG. 7 is a view along line 7-7 of FIG. 5.

Referring now to FIGS. 4 and 7, the projections 66, 68 are mirror images of each other. Each projection 66, 68 includes a partial cylindrical portion 74 projecting outwardly from the downwardly projecting tab 62 of the upper extension shell 16. At the end of the partial cylindrical portion 74 is an arced flange 76, which defines a flat inner shoulder 78 and a tapered outer shoulder 80. The arcuate length of the flange 76 is approximately 30 degrees shorter than the arcuate length of the openings 70, 72 in which the projections 66, 68 are received.

The openings 70, 72 are also mirror images of each other. Each opening 70, 72 defines a recessed shoulder 82 (best appreciated in FIGS. 4, 6, and 7) which in this embodiment extends the full arcuate length of the arcuate opening 70, 72 and which is designed to engage the flange 76 of the respective projection 66, 68 to secure the upper extension she 16 to the medial shell 14, as discussed below.

As indicated above, the arcuate length of each of the openings 70, 72 is approximately 30 degrees longer than the arcuate length of each of the projections 66, 68. This allows the upper extension shell 16 to rotate approximately 15 degrees forwardly and 15 degrees rearwardly from a neutral, straight up-and-down position, for a total of 30 degrees of rotation.

To assemble the pivoting snap-fit connection 11, the projections 66, 68 of the upper extension shell 16 are pushed outwardly through their corresponding openings 70, 72 in the medial shell 14, as shown in FIG. 7. As the projections 66, 68 are pressed outwardly into their corresponding openings 70, 72, the recessed shoulders 82 of the openings 70, 72 push in on the tapered shoulders 80 of the projections 66, 68, causing the partial cylindrical portions 74 to flex toward the center of the imaginary circle 74 (toward the axis of rotation), so the projections 66, 68 can continue to be pushed on through the openings 70, 72. Once the flanges 76 of the projections 66, 68 are past the recessed shoulder 82, the partial cylindrical portions 74 of the projections 66, 68 snap back to their original, unstressed and unflexed shape. At this point, if one were to try to pull the projections 66, 68 back out through their respective openings 70, 72, the flat inner shoulders 78 of the flanges 76 would abut the flat recessed shoulders 82 of the openings 70, 72, preventing the upper extension shell from being separated from the medial shell 14.

Once installed, the upper extension shell 16 can rotate forward and backward relative to the medial shell 14, as explained above.

When the user puts on the ankle brace 10, he tightens the straps to ensure that the brace conforms to his foot and leg. The pivotably-mounted strap 60 on the upper extension shell 16 and the upper pivot connections 11 help ensure that the upper extension shell 16 conforms to the user's leg. After the brace 10 has been installed on the user's foot and leg, there will be pivoting about the lower pivot connections 24, 26 at the ankle as the user walks, but there will be essentially no pivoting about the upper pivot connections 11.

Once the user's ankle has improved, he may wish to remove the upper extension shell 16 from the medial shell 14. The following means for disassembly may be used: To remove the upper extension shell 16, the user presses the projections 66, 68 toward each other (and toward the pivot axis) until the flat shoulders 78 of the flanges 76 have cleared the recessed shoulders 82 of the openings 70, 72. The user then pulls the upper extension shell 16 and medial shell 14 apart, pulling the projections 66, 68 in the axial direction, back through their corresponding openings 70, 72 to separate the upper shell 16 from the medial shell 14.

Thus, this releasable snap-fit pivot connection permits the user of the ankle brace 10 to convert the brace 10 to a less-restrictive configuration after the ankle has improved, by removing the upper extension shell 16 from the brace 10.

While the embodiment described above shows a simple means for pivotably securing the upper extension shell to the medial shell, various modifications may be made and other mechanisms alternatively could be used to accomplish this task.

It will be obvious to those skilled in the art that various modifications may be made to the embodiment described above without departing from the scope of the invention as claimed.

What is claimed is:

1. An ankle brace, comprising:
   a foot shell including a base for extending beneath a foot and left and right side portions extending upwardly from the base;
   a medial shell including left and right lateral walls pivotably connected to said left and right side portions of said foot shell at first and second lower pivot points, respectively; and
   an upper extension shell secured to and projecting upwardly from said medial shell along said left and right lateral walls, said upper extension shell including an upper left lateral wall pivotably connected to said left lateral wall of said medial shell, and an upper right lateral wall pivotably connected to said right lateral wall of said medial shell, wherein a first arcuate projection on one of the upper left lateral wall and the left lateral wall is received in a corresponding first arcuate opening defined on the other of said upper left lateral wall and said left lateral wall with a releasable snap fit to pivotably connect said upper left lateral wall to said left lateral wall, and wherein a second arcuate projection on one of the upper right lateral wall and the right lateral wall is received in a corresponding second arcuate opening defined on the other of said upper right lateral wall and said right lateral wall with a releasable snap fit to pivotably connect said upper right lateral wall to said right lateral wall, and wherein the first and second arcuate openings extend for a greater arcuate distance than the respective first and second arcuate projections, and the first and second arcuate openings sized and positioned so as to restrict an amount of rotation between said medial shell and said upper extension shell.

2. An ankle brace as recited in claim 1, wherein said first and second arcuate openings restrict the amount of rotation such that a total amount of rotation is not greater than 60 degrees and not less than 10 degrees.

3. An ankle brace as recited in claim 2, wherein said first arcuate projection is on the left upper lateral wall of the left upper extension and projects outwardly; and the second arcuate projection is on the right upper lateral wall of the right upper extension and projects outwardly.

4. An ankle brace as recited in claim 3, wherein said first and second lower pivot points define a first axis of rotation lying in a left-to-right vertical plane, and said first and second arcuate projections define a second axis of rotation, which lies in the same left-to-right vertical plane as said first axis of rotation.

5. An ankle brace as recited in claim 4, wherein each of said left upper and right upper lateral walls has an outer surface; wherein said first arcuate projection projects outwardly and includes a distal flange defining a flat inner shoulder and a tapered outer shoulder, with the flat inner shoulder abutting the outer surface of the respective lateral wall which defines the first arcuate opening.

6. An ankle brace as recited in claim 1, wherein each of said medial shell and said upper extension shell includes a posterior portion integral with and connecting its respective lateral walls.

7. An ankle brace as recited in claim 6, wherein said first and second arcuate openings restrict the amount of rotation such that a total amount of rotation is not greater than 60 degrees and not less than 10 degrees.

8. An ankle brace, comprising:
a foot shell including a base for extending beneath a foot and left and right side portions extending upwardly from the base;
a medial shell including left and right lateral walls pivotably connected to said left and right side portions of said foot shell at first and second lower pivot points, respectively; and
an upper extension shell secured to and projecting upwardly from said medial shell along said left and right lateral walls, said upper extension shell including an upper left lateral wall pivotably connected to said left lateral wall of said medial shell by a first snap-together pivot connection, and an upper right lateral wall pivotably connected to said right lateral wall of said medial shell by a second snap-together pivot connection;
wherein each of said first and second snap-together pivot connections includes an outwardly directed arcuate projection on the respective upper lateral wall of the upper extension and a corresponding arcuate opening defined in the respective lateral wall of the medial shell which receives the respective arcuate projection.

9. An ankle brace as recited in claim 8, wherein said first and second lower pivot points define a first axis of rotation, which lies in a left-to-right vertical plane; and said first and second snap-together pivot connections define a second axis of rotation, which lies in the same left-to-right vertical plane as said first axis of rotation.

10. An ankle brace as recited in claim 9, wherein each of said outwardly directed arcuate projections includes a flange defining a flat inner shoulder and a tapered outer shoulder.

* * * * *

UNITED STATES PATENT AND TRADEMARK OFFICE
CERTIFICATE OF CORRECTION

| | | |
|---|---|---|
| PATENT NO. | : 9,186,269 B2 | Page 1 of 1 |
| APPLICATION NO. | : 13/527653 | |
| DATED | : November 17, 2015 | |
| INVENTOR(S) | : Rick Peters | |

It is certified that error appears in the above-identified patent and that said Letters Patent is hereby corrected as shown below:

On the title page item (57), in the "Abstract", line 3, delete "was" and insert therefor --walls--

In the specification,

Column 3, line 44, delete "she" and insert therefor --shell--

Signed and Sealed this
Twelfth Day of April, 2016

Michelle K. Lee
*Director of the United States Patent and Trademark Office*